US005670139A

United States Patent [19]

Allard et al.

[11] Patent Number: 5,670,139
[45] Date of Patent: Sep. 23, 1997

[54] STABLE NANOPIGMENTED SUNSCREEN/ COSMETIC COMPOSITIONS

[75] Inventors: Delphine Allard, Colombes; Jean-Marc Ascione, Paris, both of France

[73] Assignee: L'Oreal, Paris, France

[21] Appl. No.: 391,355

[22] Filed: Feb. 21, 1995

[30] Foreign Application Priority Data

Feb. 18, 1994 [FR] France ................................. 94 01861

[51] Int. Cl.$^6$ ..................................... A61K 7/42
[52] U.S. Cl. ..................... 424/59; 424/60; 514/937; 514/938; 514/939; 514/941
[58] Field of Search ................ 424/59, 60; 514/937, 514/938, 939, 941

[56] References Cited

U.S. PATENT DOCUMENTS

| | | | |
|---|---|---|---|
| 5,032,390 | 7/1991 | Iwaya et al. | 424/59 |
| 5,093,099 | 3/1992 | Haishi et al. | 423/622 |
| 5,340,567 | 8/1994 | Cole et al. | 424/59 |

FOREIGN PATENT DOCUMENTS

| | | | |
|---|---|---|---|
| 0433086 | 6/1991 | European Pat. Off. | 424/59 |
| 0518773 | 12/1992 | European Pat. Off. | 424/59 |

*Primary Examiner*—Shelley A. Dodson
*Attorney, Agent, or Firm*—Burns, Doane, Swecker & Mathis, L.L.P.

[57] ABSTRACT

Stable and homogeneous, topically applicable sunscreen/cosmetic compositions well suited for the photoprotection of human skin and/or hair against the damaging effects of UV-A and/or UV-B irradiation, particularly solar radiation, and which display excellent transparency on the skin, comprise a storage-stable, ultrafine oil-in-water emulsion resistant to phase separation/settling, of a photoprotecting effective amount of homogeneously and finely dispersed particulates of at least one inorganic nanopigment which comprises a metal oxide, for example titanium dioxide, as well as a stabilizing amount of at least one mixed silicate which comprises alkali and/or alkaline earth metals, and further wherein the average particle size of the globules comprising the oily phase of the emulsion characteristically ranges from 100 nm to 1,000 nm.

40 Claims, No Drawings

STABLE NANOPIGMENTED SUNSCREEN/ COSMETIC COMPOSITIONS

CROSS-REFERENCE TO COMPANION APPLICATION

Copending application Ser. No. 08/386,092 [Attorney Docket No. 016800-014], filed Feb. 9, 1995 now U.S. Pat. No. 5,616,331 and assigned to the assignee hereof.

BACKGROUND OF THE INVENTION

1. Field of the Invention

The present invention relates to novel stable, fluid and/or fluidizable cosmetic compositions for topical application, for the photoprotection of the skin and/or hair against ultraviolet radiation (such compositions hereinafter simply designated "sunscreen" or "sunscreen/cosmetic" compositions), to a process for the formulation thereof and also to the use of same for the cosmetic applications indicated above.

This invention more especially relates to the aforesaid sunscreen/cosmetic compositions, having improved properties and comprising oil-in-water type emulsions (in a cosmetically acceptable vehicle or carrier) that contain, as photoprotective agents which physically block the radiation (UV reflecting and/or diffusing agents), inorganic nanopigments based on the metal oxides, especially titanium dioxide, as well as stabilizers therefor, i.e., the mixed silicates of alkali and/or alkaline earth metals.

2. Description of the Prior Art

It is well known to this art that light radiation of wavelengths of from 280 nm to 400 nm promotes tanning of the human epidermis, and that irradiation of wavelengths of from 280 to 320 nm, i.e., UV-B, causes erythema and burning of the skin which can impair the development of a natural tan; hence, such UV-B radiation must be screened from the skin.

It is also known to this art that UV-A radiation, of wavelengths from 320 to 400 nm, which tans the skin, also adversely affects it, in particular in the event of a sensitive skin or a skin continually exposed to solar radiation.

UV-A rays cause, in particular, a loss in the elasticity of the skin and the appearance of wrinkles leading to a premature aging thereof. Such irradiation promotes triggering of the erythematous reaction or enhances this reaction in certain subjects, and can even be the source of phototoxic or photoallergic reactions. Thus, it is desirable to also screen out the UV-A radiation.

Many sunscreen compositions intended for photoprotection (UV-A and/or UV-B) of the skin are known to this art, and the use of inorganic nanopigments (namely, pigments, the average size of the primary particles of which does not generally exceed 100 nm) based on the metal oxides, and especially titanium dioxide, is becoming increasingly common in light of the fact that these, when they are combined with traditional UV screening agents (principally organic compounds capable of absorbing harmful radiation), provide a very high level of protection.

For a variety of reasons, associated especially with being more pleasant to use (gentleness, softness, emollience, and the like), the sunscreen compositions currently available most typically are oil-in-water emulsions (namely, a vehicle comprising an aqueous continuous dispersing phase and an oily discontinuous dispersed phase) into which the aforesaid nanopigments have been introduced at various concentrations, where appropriate in combination with other, traditional UV screening agents. These may be present both in the aqueous phase of the emulsion and in its oily phase (also referred to as the "fatty" phase). In these traditional emulsions, which contain, in addition, emulsifying agents (or surfactants) and optionally common cosmetic additives such as perfumes, colorants, or preservatives, the size of the globules constituting the fatty phase is generally greater than several microns.

One of the major drawbacks of the known sunscreen compositions of the above type (O/W emulsion containing nanopigments), and more especially of those containing titanium dioxide $TiO_2$ nanopigments, is that, when applied to the skin in the form of a film, they whiten the skin which is cosmetically undesirable and generally disliked by the users. As the concentration of nanopigments in the emulsion is increased, this effect becomes more pronounced. To avoid this problem, it would naturally be possible to employ smaller amounts of the nanopigments, but the resulting emulsions, which would admittedly produce films displaying acceptable transparency on the skin, would then no longer afford appropriate protection in the UV range, greatly limiting the value of same.

Moreover, another difficulty presented thereby is that the traditional sunscreen emulsions based on protective nanopigments provide, after topical application to the skin, an uneven, non-homogeneous or even crude distribution of the nanopigments on the skin, which can be detrimental to the quality of the desired global photoprotective response. This poor distribution of nanopigments on the surface of the skin is often the result of a substantial lack of homogeneity (poor dispersion of the pigment in its vehicle) in the initial emulsion itself (prior to application).

Lastly, with certain of the above-indicated sunscreen emulsions, and notwithstanding the fact that they contain emulsifying agents (or surfactants), a more or less lack of stability over time is observed, which is detrimental to their preservation once packaged (storage stability). This lack of stability manifests itself, in actual practice, in more or less marked phenomena of settling of the nanopigments within the emulsion, or even of separation between the aqueous and oily phases thereof.

In FR-94/01,455 (corresponding to the aforesaid Ser. No. 08/386,092, filed Feb. 9, 1995), improved sunscreen emulsions of O/W type are described, containing inorganic nanopigments based on metal oxides, which simultaneously exhibit excellent transparency on the skin, very good efficiency in terms of protection against UV irradiation, good stability and total homogeneity both before and after application to the skin (namely, the nanopigments are very well dispersed in the initial emulsion, on the one hand, and on the skin after application on the other).

More particularly, it has thus been demonstrated that it was possible to overcome the various drawbacks associated with the use and with the presence of photoprotective nanopigments in the conventional O/W emulsions of the prior art, by employing specific "ultrafine" O/W emulsions, in which the average particle size of the globules constituting the fatty phase is within well defined limits, namely, ranging from 100 to 1,000 nm, and preferably from 100 to 500 nm, said ultrafine emulsions of O/W type themselves preferably being obtained via a phase-inversion emulsification technique.

The sunscreen formulations described in FR-94/01,455 typically have the following composition: (i) aqueous phase: from 50% to 95% by weight, preferably from 70% to 90% by weight, relative to the total weight of the formulation; (ii)

oily phase: from 5% to 50% by weight, preferably from 10% to 30% by weight, relative to the total weight of the formulation; (iii) nanopigments: from 0.5% to 40% by weight, preferably from 1% to 30% by weight, relative to the total weight of the formulation; (iv) (co)emulsifiers: from 0.5% to 20% by weight, preferably from 2% to 10% by weight, relative to the total weight of the formulation.

The above formulations are preferably obtained according to a preparative process comprising the following essential steps: (a) a fatty phase, on the one hand, and an aqueous phase, on the other, are mixed together, with stirring, in the presence of a suitably selected emulsifying system (emulsifiers of nonionic type selected, whether singly or in admixture, from among polyoxyethylenated and/or polyoxypropylenated fatty alcohols, and polyol fatty acid esters, which are optionally polyoxyethylenated and/or polyoxypropylenated, the emulsifying system preferably having an overall HLB ranging from approximately 9.5 to 11.5 and even more preferably close to 10), the mixing being carried out at a temperature above the phase inversion temperature (PIT) of the medium, such as to provide an emulsion of water-in-oil type, (b) the temperature of the emulsion thus obtained is decreased below said phase inversion temperature, whereby an ultrafine emulsion of oil-in-water type is obtained, (c) the inorganic nanopigments are introduced while step (a) is being carried out and/or after completion of step (b). All factors being otherwise equal (i.e., identical concentrations and chemical composition), sunscreen compositions are thus provided, by simply adjusting the size of the oily globules to a suitable value as indicated above, which consistently exhibit, in respect in particular of transparency on the skin, stability, homogeneity and photoprotective capacity, improved properties vis-a-vis the same sunscreen compositions not satisfying the aforesaid criterion of oil globule size.

Nonetheless, it has now been determined that the compositions described in FR-94/01,455 present the drawback, when it is sought to prepare same in the fluid state, in particular for the purpose of providing compositions which are readily vaporized, that same lack a certain stability, in the shorter or longer term, such lack of stability manifesting itself, in actual practice, in the phenomenon of progressive settling of the nanopigments within the emulsion.

SUMMARY OF THE INVENTION

Accordingly, a major object of the present invention is the provision of improved O/W type emulsions having sunscreen properties and comprising inorganic nanopigments based on metal oxides, which simultaneously display excellent transparency on the skin, very good efficacy of protection against UV irradiation, very good stability and perfect homogeneity both before and after topical application to the skin, i.e., the nanopigments are stably and very well dispersed in the initial or beginning emulsion on the one hand, and on the skin after topical application on the other.

Briefly, the present invention features the improved stabilization of the aforesaid ultrafine emulsions (100 nm<$\phi_{globules}$<1,000 nm) comprising nanopigments, by incorporating therein effective stabilizing amounts of the mixed silicates of the alkali metals and/or alkaline earth metals.

DETAILED DESCRIPTION OF BEST MODE AND PREFERRED EMBODIMENTS OF THE INVENTION

More particularly according to the present invention, it has now unexpectedly and surprisingly been determined that the introduction of the subject mixed silicates into the ultrafine emulsions admittedly causes a certain thickening of the composition (which varies depending on the amounts introduced), but since the mixed silicates are thixotropic viscosity agents, the resulting compositions may, in fact, subsequently be readily fluidized, either by a mechanical action, for example by stirring of the product immediately prior to use, or during its actual application (rubbing) onto the skin, or, alternatively, by shearing of the latter when it is transferred through the pump of a vaporizer, or by dilution with water.

Moreover, incorporation of these silicates in no way disrupts the advantageous properties which are all inherently associated with the ultrafine O/W emulsions based on nanopigments, and hence the good transparency on the skin, the good efficiency in terms of UV protection, the homogeneity both before and after application to the skin and, lastly, the absence of phase separation between the fatty and aqueous phases.

The general stabilizing effect (absence of settling, on the one hand, and of phase separation, on the other) attained via the presence of the mixed silicates in the O/W emulsions based on nanopigments is all the more unexpected and surprising since these silicates, when introduced into an ultrafine emulsion free of nanopigments, cause a very rapid phenomenon of separation between the aqueous and oily phases of the emulsion (unstable emulsion).

Thus, the present invention features novel stable, fluid and/or fluidizable cosmetic, in particular sunscreen, compositions, comprising, in a cosmetically acceptable carrier or vehicle of oil-in-water emulsion type, in which the average size of the globules constituting the oily phase ranges from 100 nm to 1,000 nm, inorganic nanopigments based on metal oxides as photoprotective agents, and which additionally contain at least one mixed silicate of alkali metals and/or alkaline earth metals.

The present invention also features the use of a mixed silicate of alkali metals and/or alkaline earth metals for the stabilization of ultrafine emulsions of O/W type containing nanopigments, as well as the corresponding stabilization technique which entails introducing at least one mixed silicate of alkali metals and/or alkaline earth metals into an ultrafine emulsion of O/W type containing nanopigments, either during the actual preparation of said emulsion or after the preparation thereof (emulsion already produced).

This invention also features a specific process for the preparation of the compositions described above.

According to the present invention, by the term "mixed silicates of alkali metals and/or of alkaline earth metals" are intended silicates of natural or synthetic origin which, besides silicon and oxygen atoms (silicate units), are composed of metal cations (which ensure chemical neutrality of the overall system) selected from at least two different alkali metals or from at least two different alkaline earth metals, or from at least one alkali metal and at least one alkaline earth metal. Such silicates have a similar chemical structure as that of hectorite (natural clay). Preferably, mixed silicates of synthetic origin are employed, since these products are actually free of or substantially free of impurities, especially of free silica. The mixed silicates are, moreover, well known to this art for their thickening and thixotropic properties.

Mixed silicates containing at least one alkaline earth metal are the preferred.

Even more preferably, mixed silicates containing at least one alkaline earth metal in combination with at least one alkali metal are employed.

The alkali metals are preferably selected from among lithium, sodium and potassium.

The alkaline earth metals are themselves preferably selected from between magnesium and calcium.

In a particularly preferred embodiment of the present invention, at least one mixed silicate of magnesium, of lithium and of sodium is employed.

These compounds are well known to this art. They may, in particular, be synthesized according to the process described in U.S. Pat. No. 3,586,478. Moreover, several are commercially available and are marketed, for example, under the trademarks LAPONITE® (LAPONITES DS, D, XLS or XLG among others) by Laporte Industries, Ltd.

The metal oxides (nanopigments) which are suitable according to this invention are per se known to this art for their photoprotective activity. Thus, they can, in particular, be selected from among titanium, zinc, iron, zirconium and cerium oxides, or mixtures thereof.

Such nanopigments of metal oxides, whether coated or uncoated, are compounds well known to this art, and are, in particular, described in EP-A-0,518,773, hereby expressly incorporated by reference. Other commercial nanopigments, not indicated above, but which are also suitable according to the present invention, are the products marketed under the trademarks UVT M 160, UVT M 212 and UVT M 262 by Kemira, and MT 100 SAS marketed by Tayca.

In a preferred embodiment of the sunscreen compositions according to this invention, inorganic nanopigments based on titanium dioxide are employed, which afford the greatest efficacy in respect of photoprotection. Moreover, it should be appreciated that the undesirable cosmetic effect of whitening of the skin referred to above is especially pronounced with this type of nanopigment. This titanium dioxide can be in a crystalline form of the rutile and/or anatase type, and/or in an amorphous or substantially amorphous form. As indicated above, this pigment can then be coated or uncoated, but it is preferable to use pigments coated, for example, with alumina and/or aluminum stearate and/or silica.

Depending on their more or less marked lipophilic or, to the contrary, hydrophilic nature, the nanopigments may be present either in the fatty phase of the emulsion or in the aqueous phase, or even in both phases at the same time.

The average size of the primary particles of the nanopigments present in the compositions according to the invention generally ranges from 5 nm to 100 nm, and preferably from 10 to 50 nm.

Of course, the sunscreen compositions of the invention can, in addition, contain one or more conventional hydrophilic or lipophilic organic sunscreen agents (absorbing agents) which are active in the UV-A and/or UV-B region. Exemplary of such additional sunscreens are 2-phenylbenzimidazole-5-sulfonic acid and salts thereof, cinnamic derivatives such as, for example, 2-ethylhexyl p-methoxycinnamate, salicylic derivatives such as, for example, 2-ethylhexyl salicylate and homomenthyl salicylate, camphor derivatives such as, for example, 3-(4-methylbenzylidene)camphor or (1,4-divinylbenzene) camphorsulfonic acid, triazine derivatives such as 2,4,6-tris [p-(2'-ethylhexyl-1'-oxycarbonyl)anilino]-1,3,5-triazine, benzophenone derivatives such as 2-hydroxy-4-methoxybenzophenone, dibenzoylmethane derivatives such as 4-tert-butyl-4'-methoxydibenzoylmethane, β,β-diphenylacrylate derivatives such as 2-ethylhexyl α-cyano-β,β-diphenylacrylate, p-aminobenzoic acid derivatives such as, for example, octyl and para-dimethylaminobenzoate, menthyl anthranilate and the sunscreen polymers and sunscreen silicones described in WO-93/04,665. Other examples of organic sunscreen agents are described in EP-A-0,487,404.

The nature of the fatty phase comprising the emulsions according to the invention is not critical, and can thus include all of the compounds which are already generally known to be suitable for the formulation of oil-in-water emulsions. In particular, these compounds may be selected, whether alone or in admixture, from among the various fats, oils of vegetable, animal or mineral origin, natural or synthetic waxes, and the like.

Exemplary oils which can constitute the fatty phase include, in particular:

(a) mineral oils such as paraffin oil and liquid petrolatum;

(b) oils of animal origin such as perhydrosqualene;

(c) oils of vegetable origin such as sweet almond oil, avocado oil, castor oil, olive oil, jojoba oil, sesame oil, groundnut oil, grape-pip oil, rapeseed oil, coconut oil, hazelnut oil, shea butter, palm oil, apricot-kernal oil, calophyllum oil, rice-bran oil, maize-germ oil, wheat-germ oil, soya-bean oil, sunflower oil, evening-primrose oil, safflower oil, passion-flower oil and rye oil;

(d) synthetic oils such as purcellin oil, butyl myristate, isopropyl myristate, cetyl myristate, isopropyl palmitate, isopropyl adipate, ethylhexyl adipate, butyl stearate, hexadecyl stearate, isopropyl stearate, octyl stearate, isocetyl stearate, decyl oleate, hexyl laurate, propylene glycol dicaprylate and esters derived from lanolic acid such as isopropyl lanolate and isocetyl lanolate, isoparaffins and poly-α-olefins.

Other oils which may be used in the emulsions according to the invention include the benzoates of $C_{12}$–$C_{15}$ fatty alcohols (Finsolv TN marketed by Finetex), fatty alcohols such as lauryl, cetyl, myristyl, stearyl, palmityl and oleyl alcohol, as well as 2-octyldodecanol, acetylglycerides, the octanoates and decanoates of alcohols and of polyols such as those of glycol and of glycerol, the ricinoleates of alcohols and of polyols such as cetyl ricinoleates, the triglycerides of fatty acids such as caprylic/capric triglycerides, triglycerides of $C_{10}$–$C_{18}$ saturated fatty acids, fluorinated and perfluorinated oils, lanolin, hydrogenated lanolin, acetylated lanolin and, lastly, silicone oils, volatile or otherwise.

Naturally, the fatty phase can also contain one or more conventional lipophilic cosmetic additives and adjuvants, in particular those which to date are typically employed for the formulation of cosmetic sunscreen compositions.

An essential characteristic of the compositions in accordance with the present invention is that the average size of the liquid particles (or globules) of the fatty phase emulsified within the aqueous dispersing phase must be within very specific limits, namely, ranging from 100 nm to 1,000 nm. Preferably, this average size ranges from 100 nm to 500 nm. Even more preferably, the size distribution of the oily globules is such that the size of most of said globules (i.e., at least 90% in numerical terms) is within the limits indicated above.

In conventional manner, the aqueous dispersing phase can comprise water, or a mixture of water and polyhydric alcohol(s) such as, for example, glycerol, propylene glycol and sorbitol, or, alternatively, a mixture of water and water-soluble lower alcohol(s) such as ethanol, isopropanol or butanol (aqueous/alcoholic solution), and it can of course also contain, in addition, conventional water-soluble cosmetic additives and adjuvants.

Among the conventional cosmetic additives and adjuvants that may be formulated into the aqueous phase and/or into the fatty phase of the emulsions according to this invention (depending on their water- and/or lipid-solubility), representative are, in particular, ionic or nonionic thickeners, demulcents, antioxidants, opacifiers, stabilizers, emollients, insect repellents, moisturizing agents, vitamins, perfumes, preservatives, fillers, sequestering agents, colorants, or any other ingredient typically employed in the field of sun- and photoprotection products.

The emulsions according to the invention typically contain, in addition, particular surfactants or emulsifiers that are necessary for the preparation of the ultrafine emulsion. This feature will be more fully described below. They can, in addition, contain specific coemulsifiers, the function of which is to decrease substantially, during the preparation of the emulsion, the amount of surfactants required to produce the emulsion.

For example, the sunscreen formulations in accordance with this invention generally have the following compositions:

(i) aqueous phase: from 50% to 95% by weight, and preferably from 70% to 90% by weight, relative to the total weight of the formulation, (ii) oily phase: from 5% to 50% by weight, and preferably from 10% to 30% by weight, relative to the total weight of the formulation, (iii) nanopigments: from 0.5% to 40% by weight, and preferably from 1% to 30% by weight, relative to the total weight of the formulation, (iv) mixed silicate(s): from 0.05% to 5% by weight, and preferably from 0.1% to 3.5% by weight, relative to the total weight of the formulation, (v) (co)emulsifier(s): from 0.5% to 20% by weight, and preferably from 2% to 10% by weight, relative to the total weight of the formulation.

They also have a viscosity which is preferably below 15,000 cps (measured on a Brookfield RVT model DV2 viscometer at 5 rev/min and with disc No. 5).

The stable compositions of the present invention may be prepared by any appropriate known technique which essentially entails the introduction, into an ultrafine O/W emulsion containing nanopigments, of mixed silicates of alkali metals and/or alkaline earth metals. They may thus be obtained either by introducing the mixed silicate or silicates into an ultrafine emulsion prepared beforehand (first variant), which may itself have been obtained by any known means (ultrasound, high-pressure mixers/homogenizers, phase inversion, or the like), or by including this silicate-introduction step into the same stage of at least one of the steps of a conventional process for the preparation of an ultrafine emulsion (second variant). In this latter variant, the emulsions obtained only differ from those which would be obtained by the same process, but without the use of silicates, by the presence alone of said silicates within said emulsions. It follows therefrom that in order to obtain emulsions in accordance with the invention which have the desired chemical composition (without silicates) and structure characteristics, it suffices to use a conventional and known process for the preparation of ultrafine O/W emulsions containing nanopigments which is known to provide emulsions having the desired characteristics, but into which process a silicate-introduction step will additionally have been included. This rule of correspondence between the emulsions not containing silicates and those which do obviously also applies, by analogy, to the first variant described above.

Notwithstanding the immediately above, a particularly preferred process for the preparation of the compositions according to the invention will now be more fully described.

This preferred process is based on the technique of preparation of O/W emulsions via phase inversion. This technique is well known to this art, and is described, in particular, in the article "Phase Inversion Emulsification" by Th. Förster et al, *Cosmetics & Toiletries*, vol. 106, pp. 49–52, December 1991. The principle of which is thus as follows: an emulsion is prepared (introduction of water into oil) at a temperature which must be above the phase inversion temperature (or PIT) of the system, namely, above the temperature at which the balance between the hydrophilic and lipophilic properties of the emulsifier(s) employed is reached. At high temperature (>PIT), the emulsion is of the water-in-oil type and, as it cools, at the phase inversion temperature, this emulsion inverts to become an emulsion which is now of the oil-in-water type, having first passed through a microemulsion state.

According to the invention, nanopigments must be present in the final ultrafine O/W emulsion. Thus, in a first embodiment of the subject preparative process, the phase inversion of the emulsion is carried out in the presence of the photoprotective nanopigments described above. In a second embodiment of this process, these nanopigments are introduced only after the emulsion resulting from phase inversion has been obtained. It is of course possible to employ both embodiments concurrently.

In accordance with the first and second variants indicated above, the mixed silicates may themselves be introduced into the medium during the actual step for effecting the phase inversion (first variant) or, preferably, after completion of this step (second variant). In this case also, the two variants may be carried out concurrently.

One of the difficulties in carrying out a process such as indicated above is presented by the appropriate selection of the emulsifying system which must be suited to the desired result.

The emulsifying systems which must thus be used according to the invention are those which indeed permit stable ultrafine emulsions resulting from phase inversion (100 nm<$\phi_{globules}$<1,000 nm) to be obtained, and in which the nanopigments are dispersed finely and homogeneously.

To this end, it has now been determined that the emulsifying systems appropriate to the present invention must be nonionic type emulsifiers, more especially selected from among polyoxyethylenated and/or polyoxypropylenated fatty alcohols (i.e., compounds obtained by reacting an aliphatic fatty alcohol such as behenyl or cetyl alcohol with ethylene oxide or propylene oxide, or an ethylene oxide/propylene oxide mixture) and fatty acid esters of polyols, which are optionally polyoxyethylenated and/or polyoxypropylenated (i.e., compounds obtained by reacting a fatty acid such as stearic acid or oleic acid with a polyol such as, for example, an alkylene glycol or glycerol or a polyglycerol, optionally in the presence of ethylene oxide or propylene oxide or an ethylene oxide/propylene oxide mixture), or mixtures thereof. Moreover, and preferably, the emulsifying system employed will possess an overall HLB (as is well known, HLB (hydrophilic-lipophilic balance in Griffin's sense; see *J. Soc. Cosm. Chem.*, vol. 5, pp. 249–256 (1954)) represents the balance between the hydrophilic character and the lipophilic character of the surfactant) ranging from 9.5 to 11.5, approximately, and advantageously is close to 10, such as to permit a phase inversion to be obtained at a temperature below 90° C. (PIT<90° C.).

It has now unexpectedly and surprisingly also been determined that the presence of the inorganic nanopigments and/or silicates in the initial system to be emulsified in no way interferes with the mechanisms which are naturally involved in a phase inversion emulsification process. To the contrary, an ultrafine emulsion is obtained in which the particles constituting the nanopigments and the mixed silicates are themselves maintained in the state of a fine dispersion (absence of agglomeration, or extremely small size of agglomerates) which is perfectly homogeneous and stable over time.

The details of a preparative process in accordance with the invention are presented in the examples below.

The present invention also features the use of the compositions according to the invention, as described above, as, or for the production of, compositions which protect the human epidermis or the hair against the damaging effects of ultraviolet irradiation, or as sunscreen compositions. The compositions may then be packaged in the form of creams, milks, cream gels, ointments, or, alternatively, fluid lotions, especially vaporizable fluid lotions. The compositions according to the invention thus present the advantageous property of being readily amenable to dilution with water, while at the same time remaining stable.

The cosmetic treatment of the skin or hair to protect same against the deleterious effects of UV rays, especially those contained in solar radiation, comprises applying thereto an effective amount of a sunscreen/cosmetic composition as described above.

In order to further illustrate the present invention and the advantages thereof, the following specific examples are given, it being understood that same are intended only as illustrative and in nowise limitative.

EXAMPLES:

Various ultrafine emulsions ($\phi_{globules}$<1 μm) containing or not containing nanopigments of $TiO_2$ and/or mixed silicates (Formulations F1 to F7) were prepared (via the phase inversion technique) and were then compared.

As regards the nanopigments, the starting materials used were as follows:

(a) nanopigmentary-grade titanium dioxide $TiO_2$, marketed under the trademark MT 100 T by Tayca, or (b) nanopigmentary-grade titanium dioxide $TiO_2$, marketed under the trademark TIOVEIL AQ by Tioxide.

The mixed silicates employed were mixed silicates of magnesium, lithium and sodium, marketed under the trademark LAPONITE XLG by Laporte Industries.

The chemical compositions (% by weight relative to the total weight of the formulation) of these formulations were as follows (see also the Table below):

| Phase A: | |
| --- | --- |
| (i) Cetyl/stearyl alcohol containing 12 mol of ethylene oxide (EUMULGIN B1 marketed by Henkel) | 3.3% |
| (ii) Glyceryl stearate (TEGIN 90 marketed by Goldschmidt) | 1.7% |
| (iii) Hydrogenated polydecene (ETHYL FLO 362 NF marketed by Ethyl Corp.) | 10% |
| (iv) Dioctylcyclohexane (Cetiol S marketed by Henkel) | 6% |
| (v) Cyclomethicone | 4% |

| -continued | |
| --- | --- |
| Phase B: | |
| (i) Titanium dioxide $TiO_2$ | from 0% to 5% |
| Phase C: | |
| (i) Mixed silicates | from 0% to 3.5% |
| Phase D: | |
| (i) Glycerol | 3% |
| (ii) Water | qs 100% |
| Phase E: | |
| (i) Preservatives | qs |

The procedure for preparing these formulations was as follows: the fatty (A) and aqueous (D) phases were both previously heated to a temperature on the order of 90° C. When the phase (B) contains the pigment referred to as MT 100 T, this pigment was introduced and dispersed into the fatty phase (A), with vigorous stirring using a MORITZ type turbo-mixer (1,000 rpm); the aqueous phase (D) was then added to the resulting dispersion, still with mechanical stirring, this emulsification step being carried out at 80° C., namely, at a temperature above the phase inversion temperature of the system. After phase inversion carried out by decreasing the temperature of the medium to about 40° C., the phase (B), when this phase contains the pigment referred to as TIOVEIL AQ, was introduced into the resulting ultrafine emulsion, followed by the phase (C) which was previously dispersed in water at 60° C., and, finally, the phase (E).

For each of the formulations thus obtained, their stability on storage was then evaluated, at room temperature (RT), on the one hand, and at 45° C., on the other, by observing the appearance or otherwise (i) of phase separation between the aqueous and oily phases of the emulsion and/or (ii) of settling of the pigment within the emulsion.

The results obtained are reported in the Table below. In this Table, the expression "OK" connotes that no phase separation and no settling were observed after storage for 2 weeks.

These results clearly demonstrate the superiority of the formulations F5 to F7 according to the invention as regards their stability.

TABLE

| FORMULATION No. | COMPOSITION | | STABILITY | |
|---|---|---|---|---|
| | Nanopigments | Silicates | at RT | at 45° C. |
| F1 (Comparative) | 0% | 0% | OK | OK |
| F2 (Comparative) | 0% | 3.5% | phase separation after 10 days | phase separation after 4 days |
| F3 (Comparative) | 5% of MT 100 T | 0% | settling after 1 day | — |
| F4 (Comparative) | 5% of TIOVEIL AQ | 0% | settling after 1 day | — |
| F5 (Invention) | 5% of MT 100 T | 3.5% | OK | OK |
| F6 (Invention) | 5% of MT 100 T | 2% | OK | OK |
| F7 (Invention) | 5% of TIOVEIL AQ | 2.5% | OK | OK |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable, stable sunscreen/cosmetic composition adopted for the photoprotection of human skin and/or hair, comprising a storage-stable, ultrafine oil-in-water emulsion of a photoprotecting effective amount of homogeneously and finely dispersed particulates of at least one inorganic nanopigment which comprises a metal oxide, and a stabilizing amount of at least one mixed silicate which comprises alkali and/or alkaline earth metals wherein the average particle size of the globules comprising the oily phase of said emulsion ranges from 100 nm to 1000 nm.

2. The sunscreen/cosmetic composition as defined by claim 1, the average particle size of the globules comprising the oily phase of said emulsion ranging from 100 nm to 500 nm.

3. The sunscreen/cosmetic composition as defined by claim 1, at least 90% of said globules having a particle size ranging from 100 nm to 1,000 nm.

4. The sunscreen/cosmetic composition as defined by claim 2, at least 90% of said globules having a particle size ranging from 100 nm to 500 nm.

5. The sunscreen/cosmetic composition as defined by claim 1, the average size of the primary particles comprising said nanopigment particulates ranging from 5 nm to 100 nm.

6. The sunscreen/cosmetic composition as defined by claim 5, the average size of the primary particles comprising said nanopigment particulates ranging from 10 nm to 50 nm.

7. The sunscreen/cosmetic composition as defined by claim 1, said at least one inorganic nanopigment comprising an oxide of titanium, zinc, iron, zirconium, or cerium, or mixture thereof.

8. The sunscreen/cosmetic composition as defined by claim 7, said at least one inorganic nanopigment comprising titanium dioxide.

9. The sunscreen/cosmetic composition as defined by claim 8, said at least one inorganic nanopigment comprising particulates of titanium dioxide coated with alumina and/or aluminum stearate and/or silica.

10. The sunscreen/cosmetic composition as defined b claim 8, said at least one inorganic nanopigment comprising a crystalline titanium dioxide.

11. The sunscreen/cosmetic composition as defined by claim 10, said at least one inorganic nanopigment comprising an amorphous titanium dioxide.

12. The sunscreen/cosmetic composition as defined by claim 1, further comprising at least one organic UV-A and/or UV-B sunscreen.

13. The sunscreen/cosmetic composition as defined by claim 1, the oily phase of said emulsion comprising a cosmetically acceptable fat, oil, wax, or mixture thereof.

14. The sunscreen/cosmetic composition as defined by claim 1, further comprising at least one emulsifying agent.

15. The sunscreen/cosmetic composition as defined by claim 14, comprising from 0.5% to 40% by weight thereof of said at least one emulsifying agent.

16. The sunscreen/cosmetic composition as defined by claim 15, comprising from 2% to 10% by weight thereof of said at least one emulsifying agent.

17. The sunscreen/cosmetic composition as defined by claim 1, the aqueous phase of said emulsion comprising water, admixture of water and at least one polyhydric alcohol, or admixture of water and at least one water-soluble lower alcohol.

18. The sunscreen/cosmetic composition as defined by claim 1, further comprising at least one cosmetically acceptable adjuvant or additive.

19. The sunscreen/cosmetic composition as defined by claim 18, said at least one adjuvant or additive comprising an ionic or nonionic thickener, demulcent, antioxidant, opacifier, stabilizer, emollient, insect repellent, hydrating agent, filler, vitamin, perfume, preservative, sequestering agent, colorant, or mixture thereof.

20. The sunscreen/cosmetic composition as defined by claim 1, the aqueous phase of said emulsion comprising from 50% to 95% by weight thereof.

21. The sunscreen/cosmetic composition as defined by claim 20, the aqueous phase of said emulsion comprising from 70% to 90% by weight thereof.

22. The sunscreen/cosmetic composition as defined by claim 20, the oily phase of said emulsion comprising from 5% to 50% by weight thereof.

23. The sunscreen/cosmetic composition as defined by claim 21, the oily phase of said emulsion comprising from 10% to 30% by weight thereof.

24. The sunscreen/cosmetic composition as defined by claim 22, the nanopigment particulates comprising from 0.5% to 40% by weight thereof.

25. The sunscreen/cosmetic composition as defined by claim 24 said nanopigment particulates comprising from 1% to 30% by weight thereof.

26. The sunscreen/cosmetic composition as defined by claim 21 the at least one mixed silicate comprising from 0.05% to 5% by weight thereof.

27. The sunscreen/cosmetic composition as defined by claim 26, said at least one mixed silicate comprising from 0.1% to 3.5% by weight thereof.

28. The sunscreen/cosmetic composition as defined by claim 1, said at least one mixed silicate comprising lithium, sodium and/or potassium values.

29. The sunscreen/cosmetic composition as defined by claim 1, said at least one mixed silicate comprising magnesium and/or calcium values.

30. The sunscreen/cosmetic composition as defined by claim 1, said at least one mixed silicate comprising at least one alkali metal.

31. The sunscreen/cosmetic composition as defined by claim 1, said at least one mixed silicate comprising magnesium, lithium and sodium values.

32. A process for the preparation of the sunscreen/cosmetic composition as defined by claim 1, comprising (i) emulsifying the aqueous phase into the oil phase thereof, at a temperature above the phase inversion temperature of the medium, (ii) cooling the water-in-oil emulsion thus obtained to a temperature below said phase inversion temperature, thereby converting said water-in-oil emulsion into said ultrafine oil-in-water emulsion, and (iii) introducing said nanopigment particulates and said at least one mixed silicate into the medium of emulsion either during the step (i) and/or after the step (ii).

33. The process as defined by claim 32, wherein step (i) is carried out in the presence of an effective emulsifying amount of at least one nonionic surfactant.

34. The process as defined by claim 33, said at least one nonionic surfactant comprising a polyoxyethylenated and/or polyoxypropylenated fatty alcohol, an optionally polyoxyethylenated and/or polyoxypropylenated fatty acid ester of a polyol, or mixture thereof.

35. The process as defined by claim 32, wherein the step (i) medium of emulsion has an overall HLB ranging from about 9.5 to 11.5.

36. The process as defined by claim 35, said overall HLB being approximately 10.

37. The sunscreen/cosmetic composition prepared by the process as defined by claim 32.

38. A method for protecting human skin and/or hair against the deleterious effects of ultraviolet irradiation, comprising topically applying thereto an effective amount of the sunscreen/cosmetic composition as defined by claim 1.

39. A method for protecting human skin and/or hair against the deleterious effects of solar radiation, comprising topically applying thereto an effective amount of the sunscreen/cosmetic composition as defined by claim 1.

40. The sunscreen/cosmetic composition as defined by claim 1, comprising a cream, gel, milk or lotion.

* * * * *